(12) United States Patent
Strauch

(10) Patent No.: US 8,499,615 B2
(45) Date of Patent: Aug. 6, 2013

(54) GAS CHROMATOGRAPH COMPRISING A CONTROLLABLE SWITCHING DEVICE

(75) Inventor: Piotr Strauch, Rülzheim (DE)

(73) Assignee: Siemens Aktiegesellschaft, Munich (DE)

( * ) Notice: Subject to any disclaimer, the term of this patent is extended or adjusted under 35 U.S.C. 154(b) by 162 days.

(21) Appl. No.: 13/133,554

(22) PCT Filed: Nov. 24, 2009

(86) PCT No.: PCT/EP2009/065693
§ 371 (c)(1),
(2), (4) Date: Aug. 22, 2011

(87) PCT Pub. No.: WO2010/066571
PCT Pub. Date: Jun. 17, 2010

(65) Prior Publication Data
US 2011/0290001 A1    Dec. 1, 2011

(30) Foreign Application Priority Data

Dec. 9, 2008  (DE) .......................... 10 2008 061 157

(51) Int. Cl.
*G01N 30/04*      (2006.01)

(52) U.S. Cl.
USPC ................ 73/23.42; 73/23.41; 95/86; 96/101

(58) Field of Classification Search
USPC ... 73/23.35, 23.41, 23.42; 95/86; 96/101–107
See application file for complete search history.

(56) References Cited

U.S. PATENT DOCUMENTS

| | | | | | |
|---|---|---|---|---|---|
| 4,124,358 | A | * | 11/1978 | Muller | 95/83 |
| 4,704,141 | A | * | 11/1987 | Krebber | 96/103 |
| 4,873,058 | A | * | 10/1989 | Arnold et al. | 422/89 |
| 5,379,629 | A | * | 1/1995 | Muller | 73/23.27 |
| 5,469,731 | A | * | 11/1995 | Decker et al. | 73/23.31 |
| 8,240,331 | B2 | * | 8/2012 | Appleby et al. | 137/527 |
| 2004/0232366 | A1 | | 11/2004 | Seeley | |
| 2011/0290001 | A1 | * | 12/2011 | Strauch | 73/23.42 |
| 2012/0131987 | A1 | * | 5/2012 | Gellert et al. | 73/23.42 |
| 2012/0242489 | A1 | * | 9/2012 | Wang et al. | 340/632 |

FOREIGN PATENT DOCUMENTS

| | | |
|---|---|---|
| DE | 28 06 123 | 8/1979 |
| DE | 28 40 612 | 3/1980 |
| DE | 37 17 456 | 7/1988 |
| DE | 199 14 358 | 10/2000 |
| GB | 978 019 | 12/1964 |
| WO | WO 00/17634 | 3/2000 |
| WO | WO 02/063290 | 8/2002 |

* cited by examiner

*Primary Examiner* — Hezron E Williams
*Assistant Examiner* — Hoang Nguyen
(74) *Attorney, Agent, or Firm* — Cozen O'Connor

(57) ABSTRACT

A gas chromatograph comprising two separating devices disposed one behind the other, and through which a material sample is conducted by a carrier gas. A pressure regulator regulates the pressure of the carrier gas introduced into the first separating device. A controllable switching device is arranged between the two separating devices. The switching device contains a main gas path lying between the two separating devices and two auxiliary gas paths, which are connected to the main gas path through connecting gas paths and are both fed with the carrier gas and contain flow resistors and a controllable valve for setting different pressure conditions. The auxiliary gas paths are supplied with the carrier gas through the same pressure regulator to reduce the design and adjustment effort in setting the pressure conditions, where fixed resistors are used for the flow resistors.

4 Claims, 1 Drawing Sheet

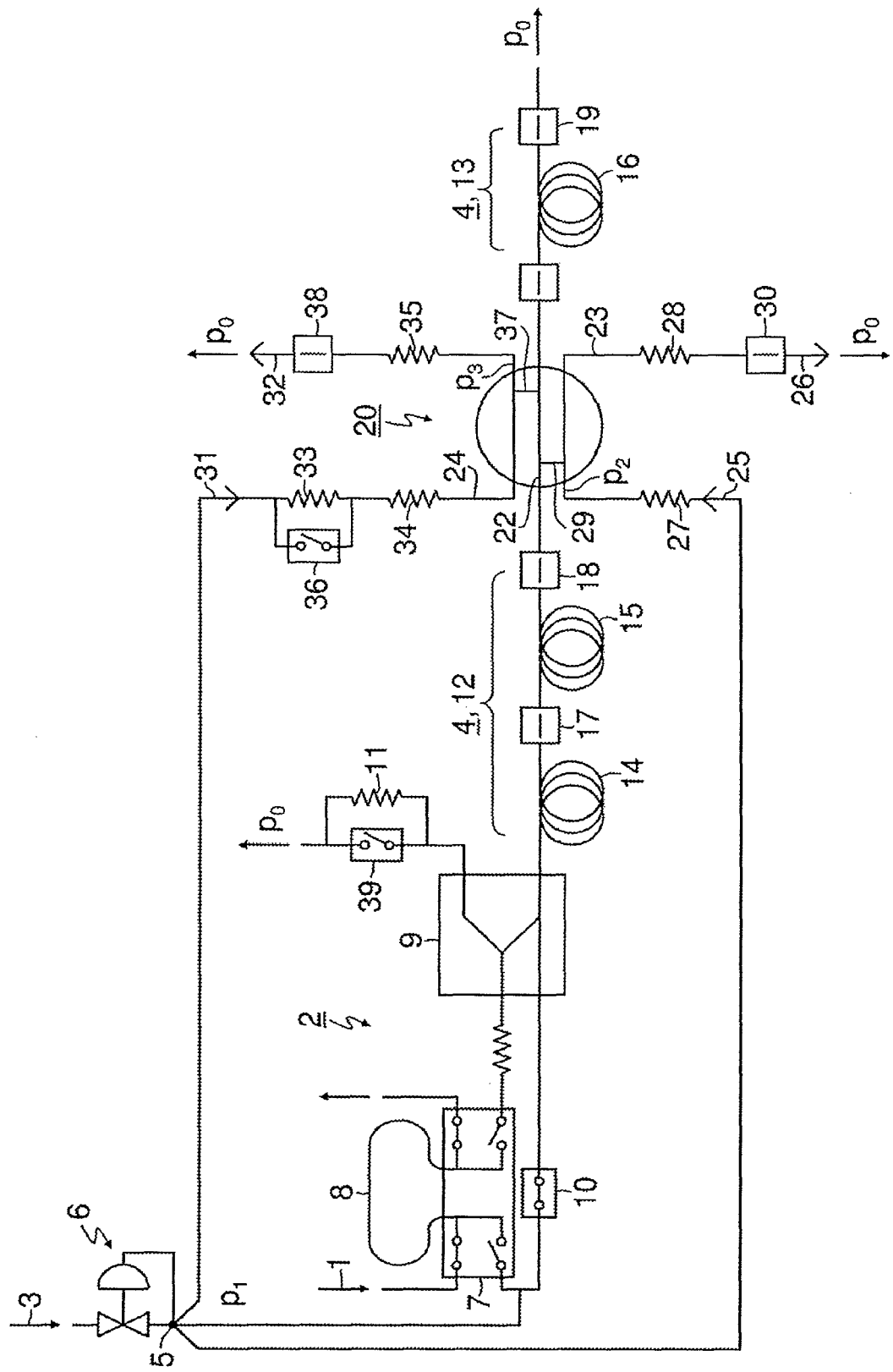

GAS CHROMATOGRAPH COMPRISING A CONTROLLABLE SWITCHING DEVICE

CROSS-REFERENCE TO RELATED APPLICATION

This is a U.S. national stage of application No. PCT/EP2009/065693 filed 24 Nov. 2009. Priority is claimed on German Application No. 10 2008 061 157.3 filed 9 Dec. 2008, the content of which is incorporated herein by reference in its entirety.

BACKGROUND OF THE INVENTION

1. Field of the Invention

The invention relates to gas chromatography and more particularly, to a gas chromatograph in which a material sample is conductable through a first separating device and subsequently conductable through a second separating device by a carrier gas.

2. Description of the Related Art

DE 28 06 123 C2 discloses one type of gas chromatograph. Here, by setting different pressure gradients between auxiliary gas paths of a switching device and between these paths and connection points of a main gas path, it is possible either to allow the components of a material sample emerging from a first separating device (i.e., separation column or separation column circuit) to enter into the second separating device or, for the operating mode (i.e., "cutting") to block entry. Here, it is possible, in the operating mode, for the components to be fed by the appropriate auxiliary gas path to a downstream detector or a third separating device. Moreover, the switching device can be used to back-flush the first separating device with a carrier gas. The switching device that is required for switching over the gas flows comes into contact only with the carrier gas, but the switching device does not come into contact with the material sample. The main, auxiliary and connecting gas paths are in the form of a multi-part construction involving capillaries, but this is relatively complex, especially as the parts have to be adjusted relative to one another.

WO 00/17634 A2 discloses a switching device structure that is considerably simpler and more planar.

DE 28 06 123 C2 and WO 00/17634 A2 show different ways of setting the pressure in the auxiliary gas paths of the switching device, but at least one dedicated pressure regulator is required in addition to the a dedicated pressure regulator for regulating the pressure of the carrier gas introduced into the gas chromatograph.

Thus, in the case of the switching device depicted in FIG. 1 of DE 28 06 123 C2, both auxiliary gas paths contain a dedicated pressure regulator, where the first auxiliary gas path additionally contains a flow resistor in the form of a needle valve and a controllable solenoid valve in parallel with the controllable solenoid valve downstream of the outlet of the associated pressure regulator. Pressure switching in the auxiliary gas paths can also be performed without the two valves, simply by adjusting the set point of the pressure regulator in the first auxiliary gas path to a higher or lower value than the value set at the pressure regulator in the second auxiliary gas path. Manual setting of the different pressures is performed iteratively in a number of steps and is correspondingly complex. If the pressure of the carrier gas introduced into the first separating device is changed in order, for example, to optimize the separation rate (i.e., measuring rate) or separation performance, the pressures to be supplied to the auxiliary gas paths by the pressure regulators have to be reset each time. In addition, each pressure regulator requires a constant load flow for regulation, which leads to a high consumption of carrier gas.

In the case of the switching device depicted in FIG. 2 of DE 28 06 123 C2, both auxiliary gas paths together have a dedicated common pressure regulator. A needle valve with a controllable solenoid valve in parallel therewith is arranged in the first auxiliary gas path, downstream of the outlet of the pressure regulator. The second auxiliary gas path likewise contains a needle valve downstream of the outlet of the associated pressure regulator. Here, manual adjustment of the needle valves to set the different pressures in the auxiliary gas paths is complex and also occurs iteratively in a number of steps. In addition, the flow resistance of needle valves is temperature-dependent and, not least for this reason, it is very difficult to set precise pressure drops accurately by needle valves. With each change in the pressure of the carrier gas introduced into the first separating device, the pressures in the auxiliary gas paths have to be reset.

SUMMARY OF THE INVENTION

It is therefore an object of the present invention to reduce the design outlay and required adjustments for setting pressure conditions in the switching device.

These and other objects and advantages are achieved in accordance with the invention by providing a gas chromatograph in which a material sample is conductable through a first separating device and subsequently conductable through a second separating device by a carrier gas, where the gas chromatograph includes a pressure regulator for regulating the pressure of the carrier gas introduced into the first separating device, and a controllable switching device for discharging components of the material sample from the path to the second separating device.

The switching device is arranged between the first and second separating devices and contains a main gas path between the first and second separating devices, and a first auxiliary gas path and a second auxiliary gas path, which are each fed with the carrier gas, and each contain a plurality of flow resistors arranged in series between an inlet and an outlet for the carrier gas, and are each connected to the main gas path by a connecting gas path between the plurality of flow resistors, In accordance with the invention, the first auxiliary gas path is connected to the main gas path at a connection point adjacent to the first separating device, and the second auxiliary gas path is connected to the main gas path at a connection point adjacent to the second separating device, and one of the two auxiliary gas paths includes a controllable valve connected in parallel with the flow resistor in a path section between the inlet thereof and the connecting gas path, where the inlets of first and second auxiliary gas paths are connected to the outlet of one pressure regulator, a further flow resistor is arranged in a path section that contains the controllable valve, in series with the controllable valve and the flow resistor which is in parallel with the controllable valve, and where the flow resistors are fixed resistors.

The gas chromatograph in accordance with the invention is thus configured to include only one pressure regulator for the carrier gas. This eliminates the outlay in terms of apparatus and control systems associated with using several pressure regulators and reduces the consumption of the carrier gas. The pressure conditions in the switching device are obtained from the resistance values of the fixed resistors in the auxiliary gas paths. For this purpose, these resistance values are determined by calculation a single time, using a computational model of the gas chromatograph, for example, and are then established in the fixed resistors. The fixed resistors are rigid pneumatic resistors which, in contrast to needle valves, are not adjustable and therefore also do not have to be adjusted, and the flow resistances of which are largely independent of temperature. If the pressure of the carrier gas that is fed to the gas chromatograph changes, the pressure conditions in the switching device remain unchanged. As a result, it becomes advantageously possible to vary the pressure of the carrier gas introduced into the first separating device by the pressure regulator to optimize the separating or measuring rate, without the need to readjust the pressure conditions in the switching device.

In an advantageous embodiment of the gas chromatograph in accordance with the invention, the controllable valve is contained in the second auxiliary gas path. As a result, when the pressure conditions in the switching device are switched over, the pressure at the connection point of the first auxiliary gas path, where connection point is adjacent to the first separating device, and hence also the pressure drop across the first separating device remain constant.

Other objects and features of the present invention will become apparent from the following detailed description considered in conjunction with the accompanying drawings. It is to be understood, however, that the drawings are designed solely for purposes of illustration and not as a definition of the limits of the invention. It should be further understood that the drawings are not necessarily drawn to scale and that, unless otherwise indicated, they are merely intended to conceptually illustrate the structures and procedures described herein.

BRIEF DESCRIPTION OF THE DRAWINGS

To explain the invention further, reference is made below to the single FIGURE of the drawing, in which:

The FIGURE is a schematic block diagram of a gas chromatograph in accordance with the invention.

DETAILED DESCRIPTION OF THE PREFERRED EMBODIMENTS

With specific reference to the figure, after being taken from a technical process and prepared, e.g., vaporized, a material sample 1 to be analyzed is fed to a metering device 2. The metering device 2 is used to introduce a predetermined metered quantity of the material sample 1 into a carrier gas stream 3 at a predetermined time, comprising a brief and sharply defined "shot" of the sample, and to feed it to a separating arrangement 4. The carrier gas 3 is made available at a predeterminable pressure $p_1$ at the outlet 5 of a pressure regulator 6. The metering device 2 has a metering valve arrangement 7, which directs the material sample 1 into a metering volume 8 in a first operating position shown, here. In a second operating position, the metering volume 8 is switched to the path for the carrier gas 3, which feeds the sample 1 from the metering volume 8 to an injector 9. As long as a solenoid valve 10 is open, the carrier gas 3 flows through the solenoid valve 10 and the injector 9 into the separating arrangement 4, while the sample 1 is discharged to the outside from the metering volume 8 by a flow resistor 11. If the solenoid valve 10 is closed for a predetermined period, part of the sample 1 is diverted in the injector 9 and is introduced into the separating arrangement 4 as a sharply defined shot of the material sample 1.

The separating arrangement 4 is used to separate the components of the material sample 1 that are contained in the shot of the sample material 1 as they flow through the separating arrangement 4 to enable them to be detected and quantitatively determined one after the other. In the example shown here, the separating device 4 comprises two successive separating devices 12 and 13 comprising separation columns 14, 15, 16 connected in series, which have different separating characteristics and are settable to different temperatures. Arranged at the end of each separation column 14, 15, 16 is a detector 17, 18, 19 for detecting predetermined components of the material sample 1 which have up to that point been completely separated.

A switching device 20 is inserted between the first separating device 12 and the second separating device 13. The switching device 20 has a main gas path 22, which connects the two separating devices 12 and 13 to one another, and a first and second auxiliary gas path 23 and 24, respectively. The first auxiliary gas path 23 has an inlet 25 connected to the outlet 5 of the pressure regulator 6 and an outlet 26 for the carrier gas 3, which is at atmospheric pressure $p_0$. Between the inlet 25 and the outlet 26 there are two flow resistors 27 and 28 arranged in series, between which the first auxiliary gas path 23 is connected to the main gas path 22 by a connecting gas path 29 at a connection point adjacent to the first separating device 12. Here, the carrier gas pressure $p_2$ at the branch for the connecting gas path 29 from the first auxiliary gas path 23 is determined in accordance with the relationship $p_1 > p_2 > p_0$. A detector 30 for components of the material sample 1 is arranged upstream of the outlet 26.

The second auxiliary gas path 24 likewise has an inlet 31 connected to the outlet 5 of the pressure regulator 6 and an outlet 32 for the carrier gas 3, which is at atmospheric pressure $p_0$. Three flow resistors 33, 34 and 35 are connected in series between the inlet 31 and the outlet 32, where a controllable valve 36 is arranged in parallel with flow resistor 33. Between flow resistors 34 and 35, the second auxiliary gas path 24 is connected to the main gas path 22 by a connecting gas path 37 at a connection point adjacent to the second separating device 13. Here, the carrier gas pressure $p_3$ at the branch for the connecting gas path 37 from the second auxiliary gas path 24 is determined in accordance with the relationship $p_1 > p_3 > p_0$. A detector 38 for components of the material sample 1 is arranged upstream of the outlet 32.

The flow resistors 27, 28, 33, 34 and 35 are fixed resistors, the resistance values of which are such that the pressure conditions are determined in accordance with the relationship $p_1 > p_2 > p_3$ when the valve 36 is closed and in accordance with the relationship $p_1 > p_3 > p_2$ when the valve is open. When valve 36 is closed, components of the material sample 1 emerging from the first separating device 12 are therefore directed over the main gas path 22 into the second separating device 13. When valve 36 is open, components of the material sample 1 emerging from the first separating device 12 are diverted from the main gas path 22, through the connecting gas path 29, into the first auxiliary gas path 23 and are discharged through the outlet 26 thereof or are fed to a third separating device (not shown), for example. Finally, with valve 36 open, the first separating device 12 can be back-flushed with the carrier gas 3 from the second auxiliary gas path 24 if, in addition, the solenoid valve 10 is closed and the flow resistor 11 at the outlet of the injector 9 is bypassed by another solenoid valve 39 in the first operating position (as shown here) of the metering valve arrangement 7.

The arrangement of the flow resistors 27, 28, 33, 34 and 35 can also be interchanged with respect to the two auxiliary gas paths 23 and 24. In the disclosed embodiment, there is the resultant advantage that the carrier gas pressure $p_2$ at the connection point of an auxiliary gas path adjacent to the first separating device 12 is constant, irrespective of the operating position of the valve 36, with the result that the pressure drop $p_1-p_2$ across the first separating device 12 and hence the separating rate/performance also remain constant.

Thus, while there are shown, described and pointed out fundamental novel features of the invention as applied to preferred embodiments thereof, it will be understood that various omissions and substitutions and changes in the form and details of the illustrated apparatus, and in its operation, may be made by those skilled in the art without departing from the spirit of the invention.

The invention claimed is:

1. A gas chromatograph in which a material sample is conductable through a first separating device and subsequently conductable through a second separating device by a carrier gas, the gas chromatograph comprising:
    a pressure regulator configured to regulate a pressure of the carrier gas introduced into the first separating device;
    a controllable switching device for discharging components of the material sample from a path to the second separating device, the switching device being arranged between the first and second separating devices and comprising:
        a main gas path between the two separating devices; and
        a first auxiliary gas path and a second auxiliary gas path, the first and second auxiliary gas paths being fed with the carrier gas, contain a plurality of flow resistors arranged in series between an inlet and an outlet for the carrier gas, and being connected to the main gas path by a connecting gas path between the plurality of flow resistors, the first auxiliary gas path being connected to the main gas path at a connection point adjacent to the first separating device, and the second auxiliary gas path being connected to the main gas path at a connection point adjacent to the second separating device, and one of the first and second auxiliary gas paths having a controllable valve connected in parallel with the flow resistor in a path section between the inlet thereof and the connecting gas path; and
    a further flow resistor arranged in a path section containing the controllable valve, in series with the controllable valve and the flow resistor in parallel with the controllable valve;
    wherein the inlet of the first and second auxiliary gas paths is connected to the outlet of the pressure regulator; and
    wherein the plurality of flow resistors and the further flow resistor are fixed resistors.

2. The gas chromatograph as claimed in claim 1, wherein the controllable valve is contained in the second auxiliary gas path.

3. The gas chromatograph as claimed in claim 1, wherein the pressure of the carrier gas introduced into the first separating device is variable by the pressure regulator to change a separating rate.

4. The gas chromatograph as claimed in claim 2, wherein the pressure of the carrier gas introduced into the first separating device is variable by the pressure regulator to change the separating rate.

* * * * *